United States Patent [19]

Severson et al.

[11] Patent Number: 5,013,644
[45] Date of Patent: May 7, 1991

[54] IDENTIFICATION OF AFRICANIZED HONEY BEES

[75] Inventors: David W. Severson, Mazomanie; Judd M. Aiken, Black Earth, both of Wis.

[73] Assignee: Wisconsin Alumni Research Foundation, Madison, Wis.

[21] Appl. No.: 129,153

[22] Filed: Dec. 7, 1987

[51] Int. Cl.$^5$ ............... C12Q 1/68; G01N 33/566; C07H 19/06; C07H 15/12
[52] U.S. Cl. ................. 435/6; 435/320.1; 536/26; 536/27; 536/28; 436/501; 436/94; 935/77; 935/78
[58] Field of Search .............. 435/320, 6; 436/501.94; 536/28, 26, 27, 28; 935/77, 78

[56] References Cited

PUBLICATIONS

Severson et al., INTL. Conf. on Africanized Honey Bees & Bee Mites, Mar. 30–Apr. 1, 1987.
Hall, PNAS (USA) 83:4874–4877 (Jul. 1986).
Blanchetot, NUC. Acids Res. 17(8):3313 (1989).
Daly, H. V. and S. S. Balling (1978) *J. Kans. Ent. Soc.*, vol. 51, pp. 857–869.
Daly, H. V., et al. (1982) *Ann. Ent. Soc. Amer.*, vol. 75, pp. 591–594.
Rinderer, et al. (1986) *Apidologie*, vol. 17, pp. 33–48.
Mestriner, M. A. and E. P. B. Contel (1972) *Genetics*, vol. 72, pp. 733–738.
Martins, E. (1977) *Biochem. Genetics*, vol. 15, pp. 357–366.
Nunamaker, R. A. and W. T. Wilson (1981) *J. Kans. Ent. Soc.*, vol. 54, pp. 704–710.
Sylvester, H. A. (1982) *J. Apic. Res.*, vol. 21, pp. 93–97.
Ayala, F. J. and J. R. Powell (1972) *Proc. Nat. Acad. Sci.*, vol. 69, pp. 1094–1096.
Carlson, D. A. and A. B. Bolton, 1984, *Bulletin of the Ent. Soc. Amer.*, vol. 30, pp. 32–35.
Moritz, R. F. A., et al., (1986) *Experimentia*, vol. 42, pp. 322–324.
Pamilo, P. (1978) *Hereditas*, vol. 88, pp. 93–99.
Ruttner, F., 1975, *Proc. XXV Int. Cong. Apic.*, pp. 325–344.
Crain, et al. (1976), *Chromosoma*, vol. 59, pp. 1–12.
Jordan, R. A. and R. W. Brosemer (1974), *J. Insect Physiol.*, vol. 20, pp. 2513–2520.
Rinderer, Thomas E. (Feb. 1986) *American Bee Journal*, pp. 98–100, 128–129.
Taylor, Jr., O. R. (Winter 1985) *Bulletin of the Ent. Soc. Amer.*, vol. 31, No. 4, pp. 14–24.
Benson, K. (Mar. 1985) *American Bee Journal*, pp. 188–191.
Cobey, S. and T. Lawrence (Sep. 1985) *American Bee Journal*, pp. 607–711.
Collins, A. M. and T. E. Rinderer (Sep. 1986) *American Bee Journal*, pp. 623–627.
Danka, R. G. and T. E. Rinderer (Oct. 1986) *American Bee Journal*, pp. 680–683.
Stibick, Jeffery N. L., (Winter 1984) *Bulletin of the Ent. Soc. Amer.*, pp. 22–26.
Page, R. E. and E. H. Erickson (1985) *Ann. Ent. Soc. Amer.*, vol. 78, pp. 149–158.
Hall, H. G. (1986) *Proc. Nat. Acad. Sci.*, vol. 83, pp. 4874–4877.

(List continued on next page.)

*Assistant Examiner*—Stephanie W. Zitomer
*Attorney, Agent, or Firm*—Quarles & Brady

[57] ABSTRACT

Africanized honey bees are identified by using a DNA probe capable of identifying a specific repeating gene sequence in the honey bee DNA which is a diagnostic characteristic of African honey bees when located on a defined restriction endonuclease fragment from bee genomic DNA. When the DNA probe is applied to an electrophoresis gel on which the restriction fragments are resolved, the probe hybridizes to the diagnostic fragment, if present. The hybridization to the repeating sequence can then be detected by detection of the marker.

23 Claims, 1 Drawing Sheet

IDENTIFICATION OF AFRICANIZED HONEY BEES

FIELD OF THE INVENTION

This invention relates generally to the use of deoxyribonucleic acid (DNA) probes and particularly to the identification of Africanized honey bees using a DNA probe.

BACKGROUND OF THE INVENTION

In 1957 a sub-species of honey bee imported from Africa was released in Brazil. Since then, the African honey bee population has spread through South and Central America to southern Mexico. The Africanzied honey bee is expected to spread northward through the southern United States along the west coast into areas with moderate winter temperatures. The African honey bee has and, it is expected, will continue to interbreed with the North American or European honey bee. Herein lies the problem.

As it is used here, the term "African honey bee" or "AHB" includes "Africanized honey bees" and is meant to include pure African honey bees or European honey bees which have crossbred with African or Africanized honey bees and have thus become Africanized, i.e., developed African honey bee traits. The Africanized bees are descended from *Apis mellifera scutellata*, whose native country is the Savanna country of eastern and southern Africa. Pure African honey bees were originally imported to Brazil in an effort to improve that country's honey production. The beekeepers desired a bee better adapted to their hot, humid, tropical climate. Rinderer, Thomas E. (February 1986) *American Bee Journal*, pp. 98-100, 128-129 However, the introduction and spread of the African bees has resulted in the near collapse of the beekeeping industry in much of the South American community.

Unlike the more docile honey bees of generally European origin (also known as the American honey bee), which are predominant in the United States beekeeping industry, the Africanized bee has several undesirable characteristics which accounts for its identification in the media as the "killer bee". The Africanized bee is known for its relatively aggressive behavior and for its failure to establish stable hive locations. Further, the Africanized bee tends to supplant the European honey bee in any given area, for reasons not completely understood. When the European and African genetic material is mixed as a consequence of interbreeding, the hybridized bees tend to lose their European traits from generation to generation, perhaps by further cross-breeding with the dominant African strains. Reference is made to the following articles for a more detailed description of the characteristics of the Africanized bee: Taylor, Jr., O.R. (Winter 1985) *Bulletin of the Ent. Soc. Amer.*, Vol. 31, No. 4, pp. 14-24; Benson, K. (March 1985) *American Bee Journal*, pp. 188-191; Cobey, S. and T. Lawrence (September 1985) *American Bee Journal*, pp. 607-611; Rinderer, T.E. (February 1986) *American Bee Journal*, pp. 98-100, 128-129; Collins, A.M. & T.E. Rinderer (September 1986) *American Bee Journal*, pp. 623-627; Danka, R.G. & T.E. Rinderer (October 1986) *American Bee Journal*, pp. 680-683.

The potential consequences of the arrival of the Africanized bee to the beekeeping industry in a country are enormous. The United States Department of Agriculture (USDA) Animal and Plant Health Inspection Service (APHIS), which is responsible for keeping undesirable pests of plants and animals out of the United States, has determined that the Africanized bees could severely affect the queen-rearing industry, cause a drop in total production of honey, increase the operating costs of beekeeping, and force many beekeepers to go out of business or drop beekeeping as a hobby due to the aggressive nature of the Africanized bees and the restrictive ordinances applied to beekeeping. Stibick, Jeffrey N.L., (Winter 1984) *Bulletin of the Ent. Soc. Amer.*, . 22-26. It has been estimated that the Amer., pp. 22-26. introduction of Africanized bees into the United States would result in an annual loss to the beekeeping industry of $26 to $58 million.

Additionally, the agricultural productivity of areas which are predominantly inhabited by Africanized bees is also expected to suffer. Pollination is the most critical phase in the production of many important food crops, and growers often rely upon honey bees to carry out pollination at a level which maximizes crop yields. The pollination value of honey bees in the U.S. alone has been estimated at $19 billion per year. Danka and Rinderer (supra).

In order to combat the migration and accidental importation of Africanized bees into northern Mexico, the United States, and Canada, commercial bee breeders will increasingly have the need to ascertain whether their bees do or do not carry Africanized genes. To accomplish this, it is important to be able to distinguish even hybridized (Africanized) bees from European bees.

The current most widely used method for identifying Africanized bees involves discriminant analysis of morphometric characteristics. Daly, H.V. and S.S. Balling (1978) *J. Kans. Ent. Soc.*, Vol. 51, pp. 857-869; Daly, H.V., et al. (1982) *Ann. Ent. Soc. Amer.*, Vol. 75, pp. 591-594; and Rinderer, et al. (1986) *Apidologie*, Vol. 17, pp. 33-48. Because Africanized bees are slightly smaller than European bees, morphometric measurements have been useful for identification of bees from distinct Africanized and European populations. However, measurements of phenotypic characters are subject to environmental influences and do not accurately identify low and intermediate levels of hybridization between the two honey bee populations and are also not statistically accurate for individual bees or very small colonies. Daly, et al. (supra).

The most commonly proposed alternative identification method is based on electrophoretic separation of discrete allozymes, i.e., slightly different enzymes that arise from alleles at the same locus. Mestriner, M.A. and E.P.B. Contel (1972) *Genetics*, Vol. 72, pp. 733-738; Martins, E., (1977) *Biochem. Genetics*, Vol. 15, pp. 357-366; Nunamaker, R.A. and W.T. Wilson (1981) *J. Kans, Ent. Soc.*, Vol. 54, pp. 704-710; and Sylvester, H.A. (1982) *J. Apic. Res.*, Vol. 21, pp. 93-97. Specific allozyme variants will approach Hardy-Weinberg equilibria within individual populations, and significant differences between non-interbreeding populations can be maintained. For example, allozymes have been successfully used as diagnostic characters for classifying individuals belonging to different non-interbreeding sibling species of *Drosophila*. Ayala, F.J. and J.R. Powell (1972) *Proc. Nat. Acad. Sci.*, Vol. 69, pp. 1094-1096. With honey bees, however, there are overlapping and freely interbreeding populations. Computer simulations suggest that the diagnostic utility of specific allozyme variants will be rapidly lost with even low levels of gene exchange between honey bee populations. Page, R.E. and E.H. Erickson (1985) *Ann. Ent. Soc. Amer.*, Vol. 78, pp. 149-158. The use of cuticular hydrocarbon analyses for identification of Africanized bees (Carlson, D.A. and A.B. Bolton, 1984, *Bulletin of the Ent. Soc. Amer.*, Vol. 30, pp. 32-35) poses similar problems. Thus, there is still a tremendous need for an accurate method to determine whether a honey bee has become Africanized. Analyses of DNA restriction fragment polymorphisms have only recently been examined as a potential method for differentiating between honey bee subspecies. Hall, H.G. (1986) *Proc. Nat. Acad. Sci.*, Vol. 83, pp. 4874-4877; Moritz, R.F.A., et al. (1986) *Experimentia*, Vol. 42, pp. 22-324. Because DNA molecules themselves are not subject to environmental influences, DNA probes offer an alternative to identification methods utilizing phenotypic characters. Further, because DNA polymorphisms are not limited to sequences expressed as proteins, they may not be as subject to evolutionary pressures. This may be especially important with honey bees because their haplodiploid mechanisms of sex determination (haploid males, diploid females) reportedly limits enzyme variability. Pamilo, P. (1978) *Hereditas*, Vol. 88, pp. 93-99.

SUMMARY OF THE INVENTION

The method of the present invention is summarized in that a distinctive DNA characteristic has been identified which distinguishes between Africanized and European bees. The characteristic is a unique restriction enzyme fragment which hybridizes to a DNA strand containing a specific non-protein encoding highly repetitive sequence. While the repetitive sequence itself occurs both in Africanzed and European honey bees, the presence of this sequence in a defined restriction enzyme fragment, as diagnosed by a hybridization assay, is indicative of Africanized bee heritage. The restriction fragment is an approximately 2.1 kilobase Hae III fragment digested and separated from the total bee DNA.

The present invention is also summarized by a probe useful in distinguishing Africanized from European bees includes a repetitive sequence found in honey bee DNA attached to a marker so that the sequence may be used as a diagnostic probe.

It is an object of the present invention to provide a method, and to provide the tools for that method, to distinguish Africanized from European bees by their actual genetic pattern. It is an advantage of the pattern found by the inventors here that the characteristic does not code for the expression of a protein and is thus less likely to be modified by environmental pressures.

The distinct "fingerprint patterns" provided by this DNA restriction fragment polymorphism and hybridization assay process suggests that this technology may become the method of choice for identification and certification of honey bee colonies as African-free. Specific DNA sequences as probes can also be used to determine the extent of Africanization in honey bees.

Further objects, features, and advantages of the invention will be apparent from the following detailed description when taken in conjunction with the accompanying drawings.

DETAILED DESCRIPTION OF THE INVENTION

Figure 1:
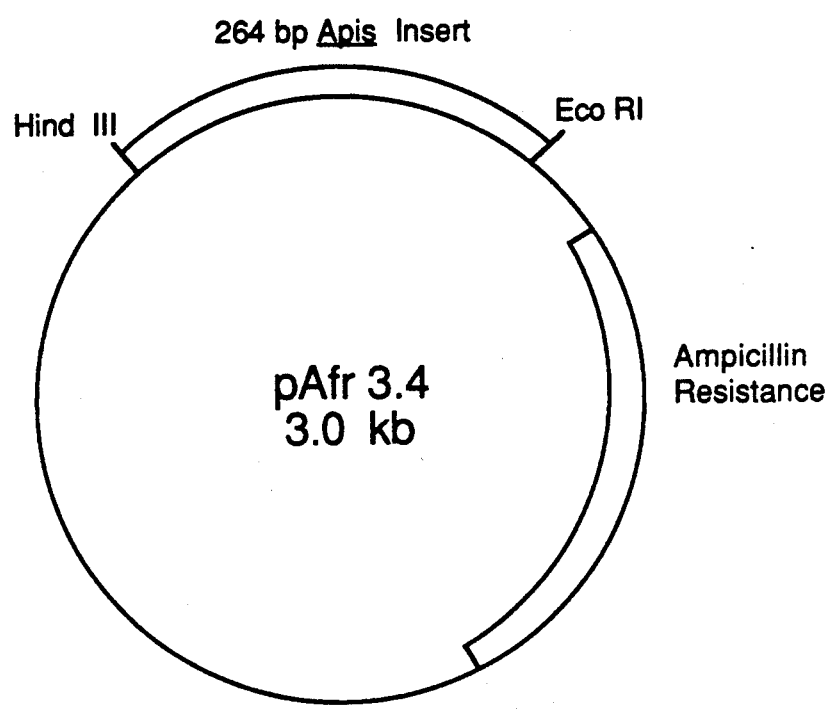
FIG. 1 is a partial restriction site and functional map for a 3.0 Kilobase plasmid p-GEM (ampicillin resistant) containing a 264 basepair Apis DNA Sau3A insert, identified as pAfr3.4, cloned into the BamHI site of the plasmid.

The present invention is directed toward a unique DNA diagnosis of Africanized bees by the detection of a repeating gene sequence in a DNA fragment created by a particular restriction enzyme digest of bee DNA. The nature of the repeating sequence, and its variations, may be recognized by examining the sequence of the pAfr3.4 plasmid, described below, and how it is used in the process here. The particular DNA fragment found to be diagnostic of Africanization, if it contains the repeating sequence, is a 2.1 Kilobase fragment of total bee DNA digested with the restriction enzyme Hae III.

The process described here thus adapts features of several more basic methods of analysis used in modern molecular biology. One step in the process is the digestion of the genome of a bee or bees with a restriction enzyme. The restriction fragments thus created are resolved by a DNA fragment separation procedure, such as agarose gel electrophoresis. The size fractionated DNA is then transferred to a solid support such as a nitrocellulose filter (*Maniatis et al.*, 1982, pp. 384-386) The filter is then analyzed by a DNA hybridization assay to ascertain if a selected or target sequence is present on the particular fragment of interest. This assay is performed, in a manner known to the art, by making a probe sequence, which is labeled with a marker, and testing whether the probe sequence will hybridize, or form a double stranded DNA molecule, with denatured, or single stranded, segments of the DNA being assayed. After washing, to remove non-hybridized DNA, the presence and location of hybridized probes can then be detected by detecting the presence of the marker moeities.

While procedures are commonly known for preparing and using DNA probes for diagnostic or other analytical purposes, the selection of a target sequence for the diagnostic or analytic probe is often difficult. The procedure thus depends critically on the nature of the DNA sequence which is the target of the probing procedure. The present procedure does not probe for a specific sequence or gene itself characteristic of Africanization in bees. Instead, the procedure makes use of a probe which hybridizes to a repeating DNA sequence common in both African and European bees. The ability of this probe to hybridize to a characteristic Hae III restriction fragment has, however, been empirically found to be indicative of Africanization of honey bees. The fact that the probe squence is a non-protein coding sequence may add to the reliability of the probe since such a sequence is less prone to adaptive change. While a particular sequence useful as the probe sequence, actually derived from the bee genome, is described and deposited here, an analysis of the sequence of the probe will reveal to those skilled in the art how various homologous oligonucleotides could be constructed to serve as the probe sequence in the method of the present invention.

The following is a description of how the process and materials of the present invention were developed and how they may be used.

1. CREATION OF DNA LIBRARIES AND CLONE SELECTION TO CREATE PROBE.

a. DNA Extraction

For all DNA extractions detailed here, honey bee genomic DNA was isolated from adult (preferably newly emerged) worker bees by homogenization in equal volumes of phenol and a lysis buffer (0.5% SDS/0.2 M NaCl/25 mM EDTA, pH 8.0). The homogenate was centrifuged and the supernatant extracted with phenol/chloroform and then ethanol precipitated following standard procedures. The nucleic acid precipitate was dissolved in water and treated with RNase A (100 ug/ml) for 30 minutes at 37° C. The solution was again phenol/chloroform extracted, ethanol precipitated and the DNA resuspended in water.

b. Library Construction

A honey bee genomic DNA library was initially constructed with DNA extracted from adult worker bees collected from an African bee colony in The Gambia.

Based on the geographic distribution of the African bee subspecies (Ruttner, F., 1975, *Proc. XXV Int. Cong. Apic.*, pp. 325-344), the Gambian bees were presumably *A.m. adansonii*. The library was screened by colony hybridization using nick-translated genomic AHB DNA. Individual colonies exhibiting the greatest hybridization intensities were selected for further analyses. Isolated clones from such colonies likely represented highly repetitive DNA sequences. Estimates suggest that 10% to 11% of the honey bee genome is comprised of sequences repeated 100 or more times. Crain, et al. (1976), *Chromosoma*, Vol. 59, pp. 1-12; Jordan, R.A. and R.W. Brosemer (1974) *J. Insect Physiol.*, Vol. 20, pp. 2513-2520.

c. Library Construction

A DNA library was constructed using standard procedures (Maniatis, et al., *Molecular Cloning: a Laboratory Manual*, Cold Spring Harbor Laboratory, (1982)). Genomic DNA obtained from 30 adult worker bees was digested with the restriction endonuclease Sau3A. Plasmid pUC9 was digested with Bam HI, treated with bacterial alkaline phosphatase, phenol/chloroform extracted, and ethanol precipitated. Honey bee DNA and plasmid were incubated together and ligated with T4 DNA Ligase. The plasmids were then transformed into *Escherichia coli* (*E. coli*), strain TBl, which had been made competent by the $CaCl_2$ method. Recombinants containing honey bee DNA inserts were identified by a lack of B-galactosidase activity in the presence of Xgal (4-Bromo-4-chloro-3-indolyl-B-D-galactopyranoside).

d. Identification of Repetitive Elements

The genomic library was screened by colony hybridization to identify clones containing repetitive DNA. Recombinant clones were grown on agar plates containing 50 microgram/ml ampicillin, and transferred to nitrocellulose circles as described by Maniatis, et al., (supra.). Total genomic honey bee DNA was labeled with (alpha $^{32}p$)-deoxycytidine by nick translation using a commercially available kit (Bethesda Research Laboratories) to a specific activity of $1-3 \times 10^8$ cpm. Nitrocellulose filters were prehybridized in a standard prehybridization solution (Maniatis, et al., supra.) containing 100 microgram/ml of yeast RNA for hour at 37° C., followed by hybridization with the heat-denatured $^{32}P$-labeled probe in the same solution for 18 hours at 42° C. Filters were washed in 2X SSC (Standard saline citrate) once at room temperature for 2 minutes and once at 42° C. for 20 minutes, and then twice at 20 minutes each in 0.3X SSC at 68° C. Autoradiography was carried out at −70° C. for 18 hours using an intensifying screen.

This hybridization procedure and conditions were used generally in other parts of the procedure below, as indicated.

e. Southern Blots

Genomic DNA, separately extracted from 5 to 10 adult worker bees from individual colonies, was digested with various restriction endonucleases including: Eco RI, Sau3A, Hae III, Hinf I, Hpa II, Alu I, Hind III, Bam HI, and Pvu II. The restriction fragments were size-fractionated on 0.6 to 1.0% agarose gels. The DNA was transferred to nitrocellulose filters by the Southern blotting technique (Southern, supra.). The filters were baked and prehybridized as described previously. Honey bee DNA inserts were isolated from recombinant plasmid by double-digestion with Eco RI and Hind III, followed by electrophoresis in a 1.0 to 1.5% low melting temperature (LMT) agarose gel. The filters were then probed with the nick-translated honey bee DNA inserts. Autoradiography was carried out at −70° C. for 4 to 12 hours using an intensifying screen.

f. Repetitive Sequences

This cloning and screening procedure was performed on the theory that repetitive sequences will provide the greatest sensitivity when used as diagnostic probes. For example, whereas honey bee DNA probes derived from single-copy sequences required up to 3 days of exposure to x-ray film before hybridization patterns were sufficiently evident (Hall, supra), the repetitive DNA probes in accordance with the present invention have been found to provide excellent hybridization patterns in as little as 4 hours.

From an initial screening of approximately 6000 colonies, 27 potential repetitive clones were isolated and tested for their diagnostic utility against various restriction endonuclease digests of genomic DNA representing African and U.S.-European colonies. The resultant hybridization patterns were identical with some clones, while other clones exhibited differential banding patterns. Clones exhibiting differential banding patterns were then tested against genomic DNA from several African and U.S.-European honey bee samples. With most of these clones, the differential banding pattern was not diagnostic for the African genotype. A specific repetitive DNA clone, pAfr3, which readily distinguishes African from U.S.-European bees was, however, isolated. The clone pAfr3 had a Apis DNA insert of about 1.2 kilobase base on comparisons with Hind III digested lambda phage DNA.

The use of repeating gene sequences as diagnostic probes is preferable to those derived from single-copy DNA sequences or from mitochondrial DNA (mtDNA). Chance mutations are more likely to be retained and maintained within a population if they occur within a repetitive sequence, because most repetitive sequences do not code for proteins or play sequence-specific roles. Flavell, R.B. (1985) In: Hohn, B. and E.S. Dennis (ed.) *Plant Gene Research: Basic Knowledge And Application. Genetic Flux In Plants.* New York, Springer-Verlag, pp. 139-156. Although mtDNA exhibits a relatively high mutation rate (Wilson, A.C., et al., 1985, *Biol. J. Linn. Soc.*, Vol. 26, pp. 375–400), the use of mtDNA probes would provide little, if any, information concerning the paternal lineage of a given worker bee because mitochondria are largely maternally inherited. (Wilson, et al., supra). A probe derived from mtDNA would, therefore, be unsuitable for identification and certification of workers from individual colonies as African-gene free. Repeating DNA sequences are also somewhat resistant to the effects of genetic recombination, whereas single-copy DNA sequences can lose their diagnostic utility after a single generation of hybridization between populations (Flavell, supra). In *Drosophila*, for example, some repetitive DNA sequences are known to be distributed over at least 1000 chromosomal regions. Wensink, et al. (1979) *Cell*, Vol. 18 pp. 1231–1246. Sequence duplication and heterogeneity can, therefore, promote inaccurate alignment during chromosome pairing and meiotic recombination, thereby maintaining repetitive sequences within progeny lines. The use of a repeating gene sequence makes an assay more sensitive than it otherwise would be. Because the probe of the present invention uses a repeating gene that is in a part of the genetic material that does not code for a protein, the gene is also believed to be insulated from evolutionary pressures.

while still containing the diagnostic repeating gene sequences would be of greater utility in the diagnosis of Africanized bee genetic material. A subcloned plasmid containing a 264 base pair probe, identified as pAfr3.4 insert or simply pAfr3.4, has been constructed using the plasmid vector pGEM-blue (Promega Biotec) and has been on deposit with the American Type Culture Collection since Nov. 5, 1987, under ATCC Accession No. 40383.

The pAfr3.4 DNA probe is a 3.0 Kilobase (kb) plasmid (ampicillin resistant) containing a 264 base pair Apis DNA Sau3A insert cloned into the BamHI site of the plasmid vector pGEM-blue. Reference is made to FIG. 1. The Apis DNA Sau3A insert can be cleaved from the vector by a HindIII plus EcoRI restriction endonuclease digestion. The insert may be separated from the vector by agarose gel electrophoresis and recovered. Five micrograms (ug) of the pAfr3.4 plasmid DNA will produce approximately 0.5 ug of DNA insert.

The nucleotide sequence of the 264 base pairs insert containing the repeating sequences which are used to diagnose Africanized bee genetic material is as follows:

```
                                          GATCAGGTCGGTTCGCCCGTTT
                                        1----------+----------+--22
                                          CTAGTCCAGCCAAGCGGGCAAA

TATACGTACCGAACAAAGTCCCCCGGTCACGTCGGTTCGACCGTTC
  23--------+----------+----------+----------+---------68
    ATATGCATGGCTTGTTTCAGGGGGCCAGTGCAGCCAAGCTGGCAAG

CGTACGTATCGGCGAAAGTCCCCCGGTCATGTCGGTTCGCCGTTC
  69-+----------+----------+----------+----------+---113
    GCATGCATAGCCGCTTTCAGGGGGCCAGTACAGCCAAGCGGCAAG

CACAGTTTCGCGCAAAGTCCCCCGGTCAGGTCGGTTCGCCCGTTC
 114-------+----------+----------+----------+---------158
    GTGTCAAAGCGCGTTTCAGGGGGCCAGTCCAGCCAAGCGGGCAAG

TATACGTACCGAACAAAGTTCCCCGGTCACGTCGGTTCGACCGTTC
 159-+----------+----------+----------+-----------+----204
    ATATGCATGGCTTGTTTCAAGGGGCCAGTGCAGCCAAGCTGGCAAG

CGTACGTATCGCGCAAAGTCCCCCGGTCAAGTCGGTTCGCCCGTTC
 205-----+----------+----------+----------+----------+250
    GCATGCATAGCGCGTTTCAGGGGGCCAGTTCAGCCAAGCGGGCAAG

TGTACGTATCGATC
 251----------+-----264
    ACATGCATAGCTAG
``` g. Subclone Library Construction

The probe pAfr3 was then examined to determine the region containing repetitive elements. This region was selected on the basis of most intense radiographic image, indicating most repeating presence in the bee genome. The DNA insert was isolated from plasmid as described previously and digested with Sau3A. Cloning conditions were as previously described except that the plasmid pGEM-blue (Promega Biotec) was used as the vector for propagation in *Escherichia coli*, strain TB1. Honey bee DNA was cloned into the Bam HI site of the plasmid.

h. Probe Development

A single stranded DNA molecule having a length less than the 1.2 kb length of pAfr3 was desired. It was believed that a probe of significantly shorter length i. Probe Alternatives

Thus a DNA probe for use in the present invention may be constructed simply by recovering the 264 base pair insert from pAfr3.4 as deposited and described above. However, many variations are possible in constructing a probe which will function in the present invention. For example, as will be described further below, various oligonucleotide probes could be constructed which would hybridize selectively to this defined Apis repeating DNA sequence. Thus the requirement for the probe is simply that it be of sufficient length and sufficient sequence homology to this repeating sequence so as to effectively selectively hybridize to this sequence under normal DNA hybridization conditions. A usually satisfactory length for such a probe is 20–25 base pairs although longer probes are often desired for increased speed and selectivity. Probes as short as 15 base pairs have also been used successfully in DNA hybridization assays. Various base pair substitutions are also possible as long as the probe, as a whole, is sufficiently homologous to effectively hybridize.

If a synthetic oligonucleotide is to be constructed, note that there are several repeating sequences in this 264 base pair insert. For example, the sequence "TAGGTA" appears at base pairs 20–30, 71–76, 161–166, 207–212 and 253–258. A longer repeating sequence, with variable sites in brackets, found at base pairs 36–51 (and others), is "[C]AAAGT[C]CCCCGGTCA." Other repeating sequences are "GTCGGTTCG" (e.g. base pairs 7–15) and CCGTT (e.g. base pairs 17–21). Thus it can be readily seen that these repeating sequences can be used as the base for oligonucleotide construction.

j. Marker

The DNA molecule or fragments of it may be labeled with detectable markers, such as radioactive or fluorescent or enzymatic markers. These marked molecules may then be used as hybridization probes to detect a chromosomal DNA fragment molecule diagnostic of Africanization of the bees.

In the preferred embodiments of the invention, the probe is labeled, e.g., with a radioactive isotope such as $^{32}P$, $^{35}S$ or $^{3}H$, which is incorporated into the DNA probe by, for example, nick-translation.

In another embodiment, the probe may be labeled with biotin, which reacts with avidin to which is bonded a chemical entity. When the avidin is bonded to the biotin, a hybrid DNA complex is formed capable of being detected, e.g., a fluorophore, an electron-dense compound capable of rendering the hybrid DNA complexes detectable by an electron microscope, an antibody capable of rendering the hybrid DNA complexes immunologically detectable, or one of a catalyst-/substrate pair capable of rendering the hybrid DNA complexes enzymatically detectable.

There are several other techniques, such as covalently bonding flourescent or enzymatic moieties to the DNA probe that may be used in the present invention. What is necessary, in some fashion, is to attach a marker to the DNA probe so that probe hybridization may be detected by detection of the marker.

2. BEE IDENTIFICATION PROCEDURE a. Isolation and Labeling of pAfr3.4 DNA Probe

The pAfr3.4 DNA insert is cleaved from the plasmid vector with appropriate restriction enzymes, i.e. with a Hind III plus EcoRI restriction endonuclease digestion. The DNA probes are then prepared by electrophoresis through low-melting point agarose gels according to the method described in Maniatis, T., et al. (1982) *Molecular Cloning: A Laboratory Manual*, Cold Spring Harbor, New York, Cold Spring Harbor Laboratory, p. 170, which is incorporated herein by reference. The honey bee insert DNA is then cut out of the gel and brought into solution with Tris-Cl and EDTA at 65° C. for 5 minutes. The agarose is removed at room temperature by three extractions. First, the melted gel slice is extracted with an equal volume of phenol. The aqueous phase is then recovered by centrifugation at 20° C, followed by reextraction with phenol/chloroform and then with chloroform. The DNA insert is then precipitated with ethanol.

The DNA insert is labeled preferably by radioisotopes using commercially available DNA labeling kits following the manufacturer's instructions. Commercial kits include, but are not limited to, the Bethesda Research Laboratories (BRL) nick translation kit, International Biotechnolgies, Inc. (IBI) nick translation kit, and IBI random priming kit. Additionally, the DNA probes of the present invention may also use non-radioactive probes, such as biotin-labeled probes probes, as described above. For the purpose of the present invention, the probe will be referenced with a radioisotope ($^{32}P$) label.

b. Collection of Honey Bee Samples

Newly emerged worker bees should be collected since older workers are subject to drifting between adjacent colonies, e.g., older worker identities are unclear. At least 20 individuals per colony should be collected. Because queen honey bees mate with several drones, a large sample size is required to provide a high probability of examining the genic contribution of each drone. Samples from each colony should immediately be frozen on dry ice for field transport and subsequently stored at $-70°$ C., or the samples can be collected and immediately placed in vials of 95% ethanol for an indefinite period.

c. Isolation of Honey Bee DNA

Honey bee genomic DNA is isolated from adult worker bees by homogenization in equal volumes of phenol and a lysis buffer (0.5% SDS/0.2 M NaCl/25 mM EDTA, pH 8.0). The homogenate is centrifuged and the supernatant extracted wih phenol/chloroform and ethanol precipitated following standard procedures. The nucleic acid precipitate is dissolved in water and treated with RNase A (100ug/ml) for 30 minutes at 37° C. The solution is again phenol/chloroform extracted, the DNA ethanol precipitated and redissolved in water.

d. Agarose Gel Electrophoresis

Approximately 0.5 to 5.0 ug honey bee DNA is digested to completion with commercially available restriction enzyme Hae III according to the manufacturer's instructions. The restriction enzyme Hae III is used to subdivide the DNA into fragments that are characteristic of both the bee genome and the particular restriction enzyme used. The preferred enzyme is restriction endonuclease Hae III (Bethesda Research Laboratories, International Biotechnologies Inc., New England Biolabs, and Promega Biotech). The DNA restriction endonuclease digestion products are size fractionated by electrophoresis on a Tris-acetate agarose gel according to the method described in Maniatis, et al. (supra. at pp. 150–161), which is incorporated herein by reference. The preferred conditions include a 1.2% gel, 24 cm. in length, run at 50 volts for 20 to 24 hours.

e. Southern Blotting

The DNA is transferred from the agarose gel to a nitrocellulose filter by the Southern blotting technique according to Southern, E.M. (1975) *J. Mol. Biol.*, Vol. 98, pp. 503–517, as described in Maniatis, et al. (supra. at pp. 384–386).

f. Hybridization

The nitrocellulose filter is first prehybridized in a solution of 50% formamide/4X Denhardts solution (1X Denhardts solution is 0.1% Ficoll/0.1% bovine serum albumin/0.1% polyvinylpyrrolidone)/4X standard saline citrate (SSC) (1X SSC is 150 mM NaCl/15 mM sodium citrate, pH 7.0)/0.1% NaDodSO4 containing 100 ug/ml of yeast RNA (0.2 ml prehybridization solution for each square centimeter of filter) for 1 hour at 37° C. The $^{32}P$ labeled probe is then boiled for 10 minutes and added to the prehybridization solution at a final concentration of $10^6$ cpm/ml. The filters are then hybridized for 12 hours at 42° C. Following hybridization, the filters are washed in 2X SSC/0.1% NaDodSO4, once at room temperature (2 minutes) and once at 42° C. (20 minutes), and then twice (20 minutes each) in 0.3X SSC/0.1% NaDodSO4 at 68° C. Autoradiography is performed as described by Maniatis, et al. (supra. at pp. 470–472).

g. Identification of Africanized Honey Bee Specific Band

When the DNA probe is applied to the nitrocellulose filter on which the size fractionated DNA fragments have been transferred, fragments containing large numbers of the repeating gene become heavily marked by the probe and thus may be identified. Africanized bees may be distinguished from the European bees by the intensities of the radiological marking of given fragments and the exact location of the fragments on the gel.

The hybridization patterns observed using pAfr3.4 insert probes provide the basis for identifying honey bee colonies of African ancestry. With U.S.-European honey bee samples, the pAfr3.4 insert probe hybridizes to several Hae III fragments: primarily the 2.4 kilobase (kb), 2.2 kb, 2.0 kb, and 1.7 kb fragments. With honey bee samples of African ancestry, hybridization of the pAfr3.4 insert probe to a 2.1 kb Hae III fragment is diagnostic. Highly African(ized) samples exhibit hybridization primarily to the 2.1 kb fragment. Samples exhibiting hybridization to the 2.1 kb fragment as well as the U.S.-European (or other) fragments represent African/European hybrids.

The following experiments are provided as illustrative of the results obtained utilizing the pAfr3.4 insert DNA probe in accordance with the invention.

EXAMPLES

Diagnostic Utility of Probe

The diagnostic utility of the clones pAfr3 and pAfR3.4 probe against Hae III digests of genomic DNA representing African colonies from The Gambia and U.S.-European colonies has been tested. The U.S.-European samples were obtained from a closed population (CP) of honey bees. The CP was established with 25 queens obtained from queen breeders throughout the major queen rearing areas of the United States and was maintained for four years prior to sample collection for DNA analysis. These bees should, therefore, be fairly representative of the genetic variation in the U.S.-European honey bee population.

Population-specific hybridization patterns were observed with the clone pAfr3 relative to several Hae III fragments. With the CP samples, the pAfr3 (and pAfr3.4) hybridized to several Hae III fragments: primarily the 2.4 kilobase (kb), 2.2 kb, 2.0 kb, and 1.7 kb fragments. Further, there was considerable variability between these samples in the hybridization intensities of the individual bands. This suggests that considerable sequence heterogeneity exists within the U.S.-European population with respect to the clone sequences. With the African samples, the clone pAfr3.4 insert hybridized primarily to a single 2.1 kb fragment. The evidence, therefore, indicates that hybridization to the 2.1 kb fragment is diagnostic for the African genome. No evidence of hybridization to the 2.1 kb fragment was observed in the CP samples.

The diagnostic utility of pAfR3.4. insert for identification of Africanized bees was tested in a blind evaluation of bee samples from Costa Rica. Specific hybridization to the 2.1 kb Hae III fragment was consistent within samples obtained from colonies identified as Africanized. Further, in addition to hybridization to the 2.1 kb fragment, hybridization to the U.S.-European-specific fragments as well as several Costa Rican-unique fragments was observed in several samples. This phenomena may reflect the level of African-European hybridization within individual colonies. Specificity of hybridization to the 2.1 kb Hae III fragment DNA from Africanized bees was subsequently tested and confirmed against samples obtained from Mexico and Colombia.

These results demonstrate the need for recombinant DNA analyses of honey bee population structure in Africa. Based on the geographic distribution of the African bee subspecies (Ruttner, supra.), bees from The Gambia are presumably *A.m. adansonii*, while bees imported into Brazil were *A.m. scutellata*. Hybridization to the 2.1 kb Hae III fragment is, however, consistent in the African and Africanized bee samples of the present experiments. Some of these Africanized bee samples are essentially indistinguishable from African bees.

Restriction Mapping of Clone pAfr3.4

Clone pAfr3 represents a honey bee DNA insert of about 1.2 kb, based on comparisons with Hind III-digested lambda phage DNA marker. To determine which portion(s) of the insert represented repetitive regions, the isolated fragment was digested with Sau3A and a subclone library was constructed with the resultant fragments. The fragment likely reflects a partial Sau3A digest during genomic library construction. The restriction digest indicated the presence of four Sau3A restriction sites internal to the original pAfR3 insert. The diagnostic utility of each subclone was tested against Hae III digest of genomic DNA representing African and U.S.-European colonies. Hybridization patterns diagnostic for the African genotype were observed with two of the subclones. Therefore, only a portion of clone pAfr3 represents repetitive DNA. Further, although the subclones exhibited hybridization patterns similar to that observed with intact clone Afr3, they differ in fragment length. One subclone represents a honey bee DNA insert of about 264 base pairs (bp), while the other represents an insert of about 78 bp. The probe pAfr3.4 includes the 264 base pair subclone from pAfr3 which retains the assay specificity. The data suggest that other variations on the pAfr3.4 probe insert are possible within the present process.

It is understood that the invention is not confined to the particular construction and arrangement herein illustrated and described, but embraces such modified forms thereof as come within the scope of the following claims.

We claim:
1. A method of identifying Africanized bees comprising the steps of:
   (a) obtaining samples of honey bees;
   (b) isolating the DNA for the sample bees;

(c) digesting the DNA from the sample bees with restriction enzyme Hae III to cut the DNA in a distinctive pattern of fragments;

(d) separating the fragments from each other;

(e) exposing the fragments to a DNA probe of at least 15 nucleotides having sufficient sequence homology to at least a portion of the 264 base pair Apis DNA insert in pAfr3.4, ATCC Accession No. 40383, to allow the probe to hybridize to repeating sequences present on the DNA fragments forming hybrid DNA complexes, and (f) detecting among the hybrid DNA complexes an approximately 2.1 kilobase fragment as an indication of the presence in the samples of a DNA sequence characteristic of Africanized bees.

2. The method according to claim 1 wherein said probe is labeled with a detectable marker.

3. The method according to claim 2 wherein the marker is selected from the group consisting of a radioactive, fluorescent, and enzymatic marker.

4. The method according to claim 3 wherein the probe is labeled with a radioactive isotope.

5. The method according to claim 4 wherein the radioactive isotope is $^{32}P$ which has been incorporated into the probe by nick-translation.

6. The method according to claim 4 wherein the radioactive isotope is selected from the group consisting of $^{32}P$, $^{35}S$ or $^{3}H$, which has been incorporated into the probe by nick-translation.

7. The method according to claim 2 wherein the marker is biotin which is selectively bonded to avidin to which is bonded a chemical entity which, when the avidin is bonded to the biotin on the hybrid DNA complex, is capable of being detected.

8. The method according to claim 1 wherein the DNA fragments are separated according to size by electrophoresis on an agarose gel.

9. The method according to claim 8 wherein the DNA fragments are separated according to size by electrophoresis on 1.2% Tris-acetate agarose gel approximately 24 cm in length, at a power of 50 volts for between 20 and 24 hours.

10. The method according to claim 8 wherein the DNA fragments are transferred by the Southern blotting technique.

11. The method according to claim 1 wherein the fragments are prehybridized in a prehybridizing solution.

12. The method according to claim 11 wherein the DNA probe is labeled with a detectable marker, denatured and added to the prehybridizing solution containing the DNA fragments at a concentration sufficient to allow the probe to hybridize to the repeating sequence.

13. The method according to claim 12 wherein the probe hybridizes to the repeating sequence for approximately 12 hours at approximately 4° C. prior to detecting the hybrid DNA complexes.

14. The method according to claim 12 wherein the detectable marker is selected from the group consisting of a radioactive, fluorescent, and enzymatic marker.

15. The method according to claim 12 wherein the detectable marker is selected from the group consisting of $^{32}P$, $^{35}S$, and $^{3}H$ radioactive isotopes.

16. The method according to claim 15 wherein the hybrid DNA complexes are autoradiographically detected.

17. The method according to claim 1 wherein the probe is at least 20 nucleotides in length.

18. The method according to claim 1 wherein the probe is an Apis DNA insert on a plasmid vector pAfr3.4, the plasmid being deposited at the ATCC Accession No. 40383.

19. A probe for use in the diagnosis of Africanization of honey bees comprising:
   a DNA sequence of at least 15 base pairs having substantial sequence homology to at least a portion of the 264 base pair Apis DNA insert in pAFR3.4, ATCC Accession No. 40383, to permit effective hybridization and
   a marker attached to the DNA sequence so that the hybridization of the DNA sequence to a complementary sequence can be detected.

20. A probe as claimed in claim 19 wherein the marker is selected from the group consisting of radioactive, fluorescent and enzymatic markers.

21. A probe as claimed in claim 19 in which the marker is selected from the group consisting of $^{32}P$, $^{35}S$ and $^{3}H$.

22. The plasmid vector pAfr3.4, ATCC Accession No. 40383.

23. A kit for use in the diagnosis of Africanization of honey bees comprising:
   a quantity of the restriction enzyme Hae III;
   a quantity of a DNA probe which comprises (i) a DNA sequence of at least 15 nucleotides having substantial sequence homology to the Apis DNA insert in pAfr3.4, ATCC Accession No. 40383, and (ii) a marker so that hybridization of the probe can be detected.

* * * * *